(12) United States Patent
Do Coutto (10) Patent No.: US 11,826,299 B2
(45) Date of Patent: *Nov. 28, 2023

(54) FINGER-SPLINTING SHEATH DEVICE AND METHOD

(71) Applicant: Lynnda Rachel Do Coutto, Cardiff, CA (US)

(72) Inventor: Lynnda Rachel Do Coutto, Cardiff, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/988,420

(22) Filed: Nov. 16, 2022

(65) Prior Publication Data

US 2023/0084063 A1 Mar. 16, 2023

Related U.S. Application Data

(63) Continuation of application No. 16/790,002, filed on Feb. 13, 2020, now Pat. No. 11,540,972.

(60) Provisional application No. 62/805,231, filed on Feb. 13, 2019.

(51) Int. Cl.
| | |
|---|---|
| *A61H 19/00* | (2006.01) |
| *A61H 7/00* | (2006.01) |
| *A61F 2/00* | (2006.01) |
| *A61B 42/20* | (2016.01) |

(52) U.S. Cl.
CPC ............ *A61H 19/40* (2013.01); *A61B 42/20* (2016.02); *A61F 2/0009* (2013.01); *A61H 7/001* (2013.01); *A61H 2201/0153* (2013.01); *A61H 2201/1253* (2013.01)

(58) Field of Classification Search
CPC .................. A61H 19/00; A61H 7/001; A61H 2201/0153; A61H 2201/1253; A61B 42/20; A61F 2/0009

See application file for complete search history.

(56) References Cited

U.S. PATENT DOCUMENTS

| | | | | |
|---|---|---|---|---|
| 4,993,433 | A * | 2/1991 | Reddy ..................... | A61F 6/04 128/842 |
| 11,540,972 | B2 * | 1/2023 | Do Coutto ............. | A61H 7/001 |
| 2009/0210027 | A1 * | 8/2009 | Wise .................. | A61N 1/36007 607/46 |

* cited by examiner

*Primary Examiner* — Samuel G Gilbert
(74) *Attorney, Agent, or Firm* — CP LAW GROUP PC; Cy Bates (57) ABSTRACT

A finger-splinting sheath device is provided for use as a self-treatment aid in assisting a bowel in a patient suffering from complications of pelvic organ prolapse, namely rectocele. The finger-splinting sheath device generally includes a monolithic molded body including a flange-element, and a sheath-element having a proximal end and a distal end, wherein the sheath-element is coupled to the flange-element at the proximal end and is closed at the distal end. The sheath-element generally includes an elliptical cross-section configured to receive two-fingers therein, wherein the sheath-element functions to splint the two fingers during use. A method for using the device includes inserting the device with two fingers within the sheath-element into the vagina and applying pressure to the vaginal walls to assist a bowel movement.

17 Claims, 7 Drawing Sheets

PROVIDING A FINGER-SPLINTING SHEATH DEVICE HAVING A FLANGE-ELEMENT AND A TUBULAR SHEATH-ELEMENT EXTENDING THEREFROM

↓

WITH UP TO TWO FINGERS INSIDE THE TUBULAR SHEATH-ELEMENT OF THE DEVICE, INSERTING THE DEVICE INTO THE VAGINA AND APPLYING PRESSURE TO THE VAGINAL WALL, WHEREBY A BOWEL MOVEMENT IS COMPLETED.

FINGER-SPLINTING SHEATH DEVICE AND METHOD

CROSS-REFERENCE TO RELATED APPLICATIONS

This application claims benefit of priority with U.S. Provisional Application Ser. No. 62/805,231, filed Feb. 13, 2019; the entire contents of which are hereby incorporated by reference.

BACKGROUND

Field of the Invention

The invention relates generally to medical devices and methods; and more particularly, to a finger-splinting sheath device and related method for self-management of complications associated with pelvic organ prolapse.

Description of the Related Art

Individuals diagnosed with pelvic organ prolapse, particularly rectocele, currently suffer from a difficulty in allowing themselves to have a successful bowel movement. Current recommendations for managing their condition include inserting fingers into the vagina and applying pressure against the vaginal walls so that a bowel movement may be assisted, this is often referred to as "digitation". Women suffering from this condition already suffer from weakened vaginal walls and connective tissue. Proper and comfortable digitation is important for managing and avoiding worsening of their condition over time.

SUMMARY

A finger-splinting sheath device is provided for use as a self-treatment aid in assisting a bowel movement in a patient suffering from complications of pelvic organ prolapse, namely rectocele. The finger-splinting sheath device generally includes a monolithic molded body including a flange-element, and a sheath-element having a proximal end and a distal end, wherein the sheath-element is coupled to the flange-element at the proximal end and is closed at the distal end. The sheath-element generally includes an elliptical cross-section configured to receive two-fingers therein, wherein the sheath-element functions to splint the two fingers during use. A method for using the device includes inserting the device with two fingers within the sheath-element into the vagina and applying pressure to the vaginal walls to assist a bowel movement.

BRIEF DESCRIPTION OF THE DRAWINGS

These and other features of the invention will become apparent to one having the ordinary level of skill in the art upon a thorough review of the following details and descriptions, particularly when reviewed in conjunction with the drawings, wherein.

DETAILED DESCRIPTION

For purposes of explanation and not limitation, details and descriptions of certain preferred embodiments are hereinafter provided such that one having ordinary skill in the art may be enabled to make and use the invention. These details and descriptions are representative only of certain preferred embodiments, however, and a myriad of other embodiments which will not be expressly described will be readily understood by one having skill in the art upon a thorough review of the instant disclosure. Accordingly, any reviewer of the instant disclosure should interpret the scope of the invention only by the claims, as such scope is not intended to be limited by the embodiments described and illustrated herein.

Advantages of the Device

The finger-splinting sheath device as-described herein is generally configured to receive human fingers within the sheath-element of the device and provides a semi-rigid structure (rigid compared to fingers alone, but still flexible in nature, for example Shore A60 durometer) to be inserted into the vagina. The device supports the vaginal canal such that when bearing down during a bowel movement, the internal muscles and connective tissues are supported against the semi-rigid structure of the device. The device also does not further weaken internal tissues and it gives temporary internal support during a bowel movement. The device keeps weakened vaginal walls from allowing the rectum to bubble inward and collect stool into the bulge, which would otherwise occur without sufficient support within the vagina. The device is also more amendable and convenient for women with long nails or jewelry on their fingers. Moreover, the device provides a more hygienic and eco-friendly option over alternatives.

Device Structure and Function

Now turning to the drawings, a preferred embodiment of the finger-splinting device is illustrated in FIGS. 1-7.

Figure 1:
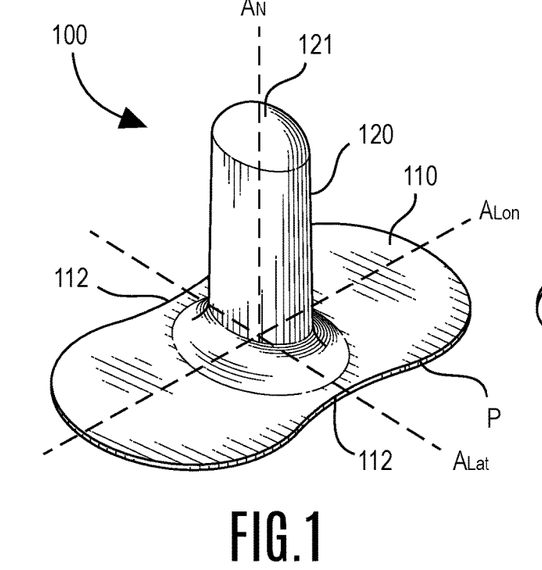
FIG. 1 is a perspective view of a finger-splinting sheath device in accordance with a preferred embodiment.

FIG. 1 provides a perspective view of a finger-splinting sheath device (100) in accordance with a preferred embodiment.

Here, the finger-splinting sheath device, or more simply the "device (100)", is shown comprising: a flange-element (110) having an aperture (111, FIG. 2) at a center thereof, and a tubular sheath-element (120) extending from the aperture of the flange element to a distal end (121), wherein the tubular sheath-element is closed at the distal end.

In the preferred embodiment, as illustrated in FIGS. 1-7, the flange-element further comprises: a length (L) defined along a longitudinal axis ($A_{Lon}$), a width (W) defined along a lateral axis ($A_{Lat}$), and a periphery (P) having an hourglass-shape with indentations (112) of the periphery being disposed along the lateral axis as shown. The indentations of the flange-element may allow the device to fit between legs of the user, or even be supported or stabilized therebetween.

Figure 7:
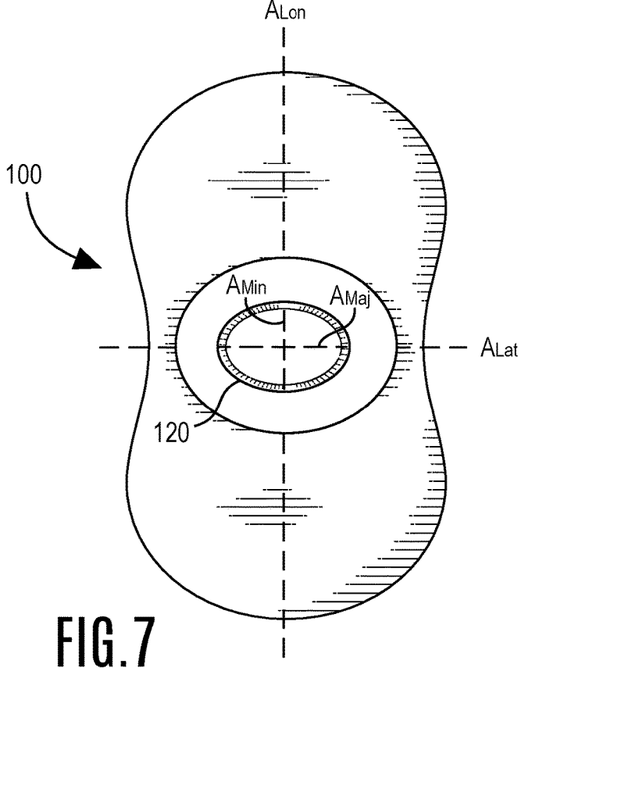
FIG. 7 is a top view of the finger-splinting sheath device with a portion of the sheath-element being sectioned to expose features thereof.

Moreover, the tubular sheath-element (120) further comprises an elliptical cross-section (See FIG. 7) taken along a normal axis ($A_{Lat}$) extending orthogonal to each of the longitudinal axis and lateral axis. The elliptical cross-section is shown in FIG. 7 comprising a major axis ($A_{Maj}$) and a minor axis ($A_{min}$), wherein, with the tubular sheath element extending orthogonal from the flange-element, the major axis is aligned in parallel with the lateral axis of the flange-element and the minor axis is aligned in parallel with the longitudinal axis. In this regard, the sheath-element is configured to receive up to two human fingers therein, with the fingers being aligned along each of: (i) the lateral axis of the flange-element and (ii) the major axis of the elliptical cross-section of the tubular sheath-element. It should be noted that the tubular sheath-element is hollow, thereby enabling the insertion of up to two human fingers within a hollow cavity therein.

Figure 2:
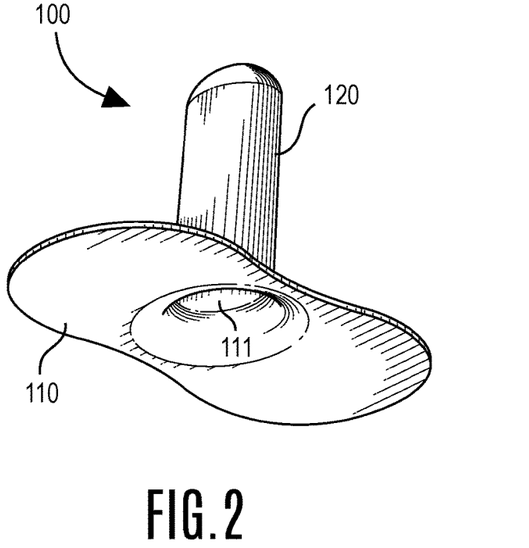
FIG. 2 is another perspective view of the finger-splinting sheath device in accordance with the preferred embodiment.

FIG. 2 is another perspective view of the finger-splinting sheath device in accordance with the preferred embodiment. Here, the aperture (111) can be more clearly visualized and appreciated. As described above, the tubular sheath-element extends from the aperture of the flange-element to a distal end, wherein the tubular sheath-element is closed at the distal end to prevent communication of fluid or other biological matter. In this regard, the human fingers, when inserted within the hollow cavity (122) of the tubular sheath-element (internal space of sheath-element), are isolated from biological material and sensitive organs.

Figure 3:
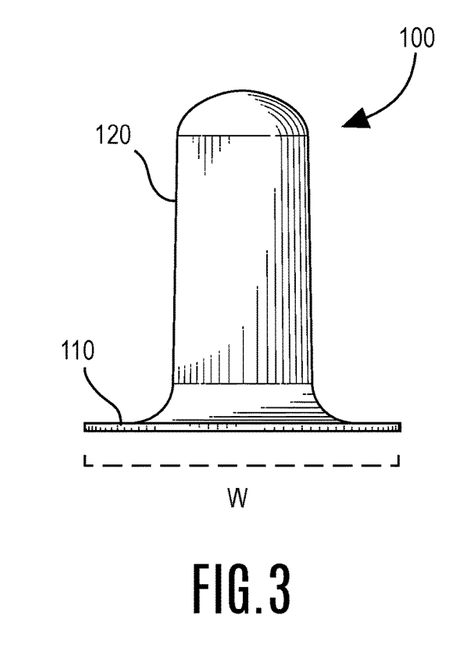
FIG. 3 is a front view of the finger-splinting sheath device in accordance with the preferred embodiment, the rear view (unshown) is a mirror opposite.

FIG. 3 is a front view of the finger-splinting sheath device in accordance with the preferred embodiment, the rear view (unshown) is a mirror opposite. Because of the symmetrical nature of the device, the rear view would look no different than that shown in FIG. 3. Here, the width (W) of the flange-element is more clearly viewed and appreciated. Also, it can be appreciated that the thickness of the sheath-element is relatively greater along the lateral axis than the corresponding thickness shown in FIG. 4 taken along the longitudinal axis; this is further shown in FIG. 7 with reference to the major and minor axes.

Figure 4:
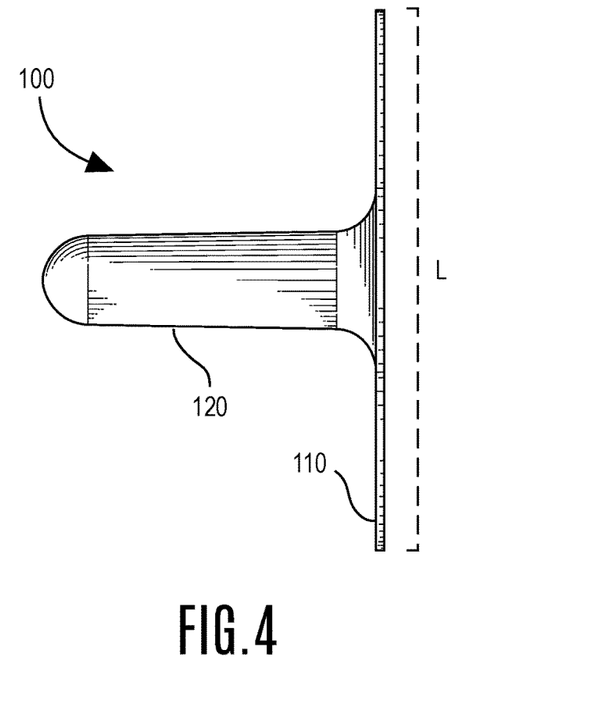
FIG. 4 is a left view of the finger-splinting sheath device in accordance with the preferred embodiment, the right view (unshown) is a mirror opposite.

FIG. 4 is a left view of the finger-splinting sheath device in accordance with the preferred embodiment, the right view (unshown) is a mirror opposite. Because of the symmetrical nature of the device, the right view would look no different than that shown in FIG. 4. With reference to FIGS. 3-4, the thickness of the tubular sheath-element is greater in FIG. 3 (along the lateral axis) than in FIG. 4 (along the longitudinal axis).

Figure 5:
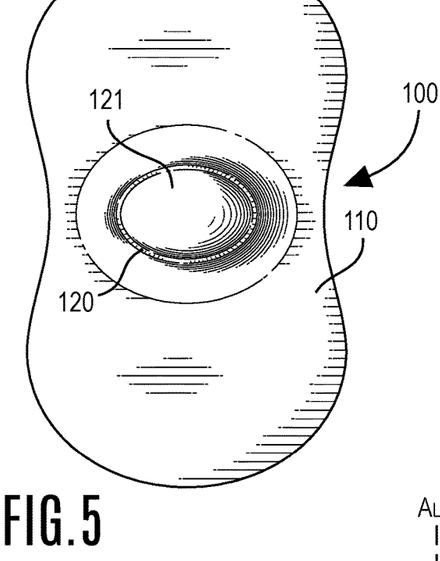
FIG. 5 is a top view of the finger-splinting sheath device in accordance with the preferred embodiment.

FIG. 5 is a top view of the finger-splinting sheath device in accordance with the preferred embodiment. From this view it can be appreciated that the distal end (121) of the tubular sheath-element (120) is closed.

Figure 6:
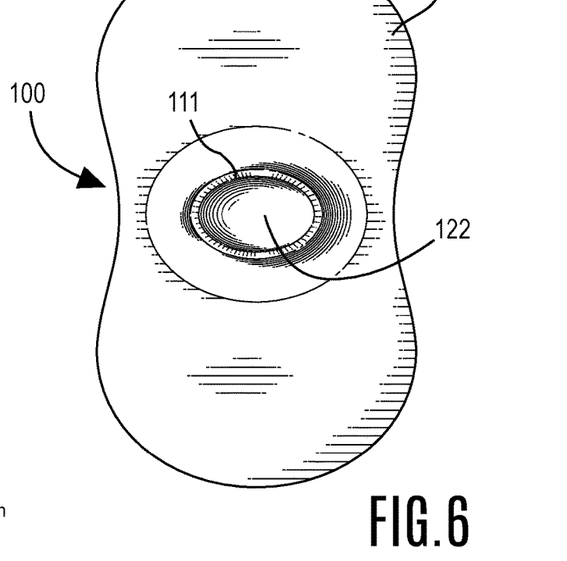
FIG. 6 is a bottom view of the finger-splinting sheath device in accordance with the preferred embodiment.

FIG. 6 is a bottom view of the finger-splinting sheath device in accordance with the preferred embodiment. Here, the aperture (111) and hollow cavity (122) within the tubular sheath-element are visualized and appreciated.

The device may be embodied in a monolithic single piece. In this regard, the device may comprise a thermoplastic elastomer material that can be injection molded, cast, or otherwise manufactured in accordance with known techniques. Examples of thermoplastic elastomers include, without limitation, di- and tri-block hydrogenated styrene block copolymers (Tekron, Elexar, and Monprene), thermoplastic polyolefin blends (Telcar), thermoplastic vulcanizates (Uniprene), and over-molding compositions designed to bond to diverse polar substrates (Tekbond). In other embodiments, the device may be fabricated from silicone or silicone-containing materials. One having skill in the art will appreciate a myriad of other materials with suitable flexibility for use in manufacturing the disclosed device.

The tubular sheath-element is mechanically biased to extend along the normal axis, wherein the normal axis is orthogonal to each of the longitudinal and lateral axes. In this regard, the normal axis is illustrated with respect to the longitudinal and lateral axes in FIG. 1.

In some embodiments, the length (L) of the flange-element may be up to two-times the width (W) of the flange-element. Similarly, the thickness of the sheath-element at the major axis of the elliptical cross-section may be up to two-times the thickness of the sheath-element at the minor axis.

Method for Using the Device

Figure 8:
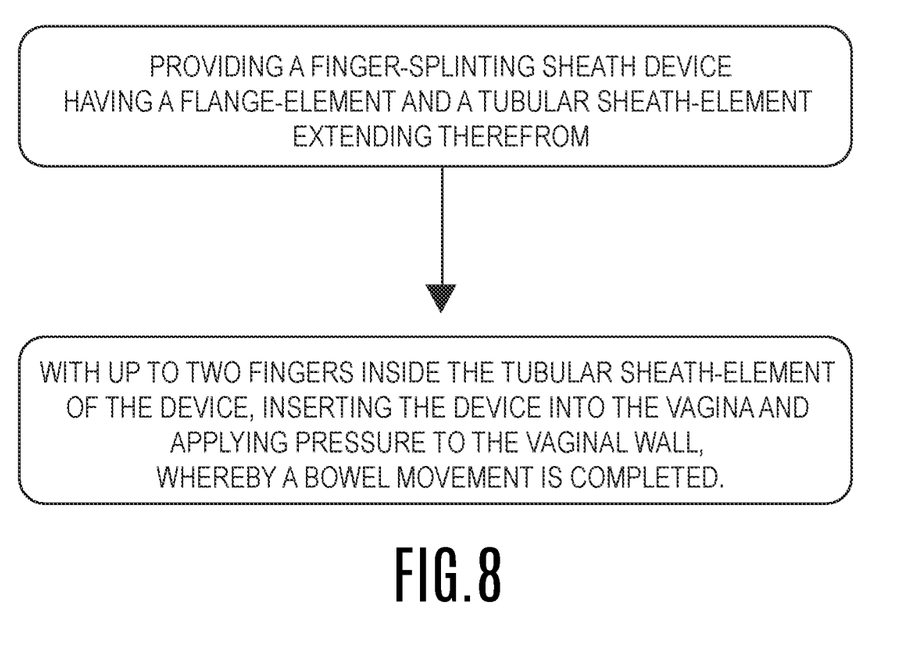
FIG. 8 is a schematic illustrating an exemplary method for using the finger-splinting device.

In another aspect of the invention, a method for effectuating a bowel movement in a patient suffering from complications of pelvic organ prolapse, namely rectocele, comprises: (i) providing the finger-splinting sheath device described herein, and (ii) with up to two fingers inside the tubular sheath-element of the device, inserting the device into the vagina and applying pressure to the vaginal wall, whereby the bowel movement is completed. FIG. 8 is a schematic illustrating the above method for using the finger-splinting device.

System Incorporating the Device and a Handle

In another embodiment, as illustrated in FIGS. 9-12, a system is disclosed for use as a self-treatment aid in assisting a bowel movement in a patient suffering from complications of pelvic organ prolapse, namely rectocele. The system generally comprises the finger-splinting device (100) as described above, and a handle assembly (200) for manipulating the device and enabling finger-less digitation.

Figure 9:
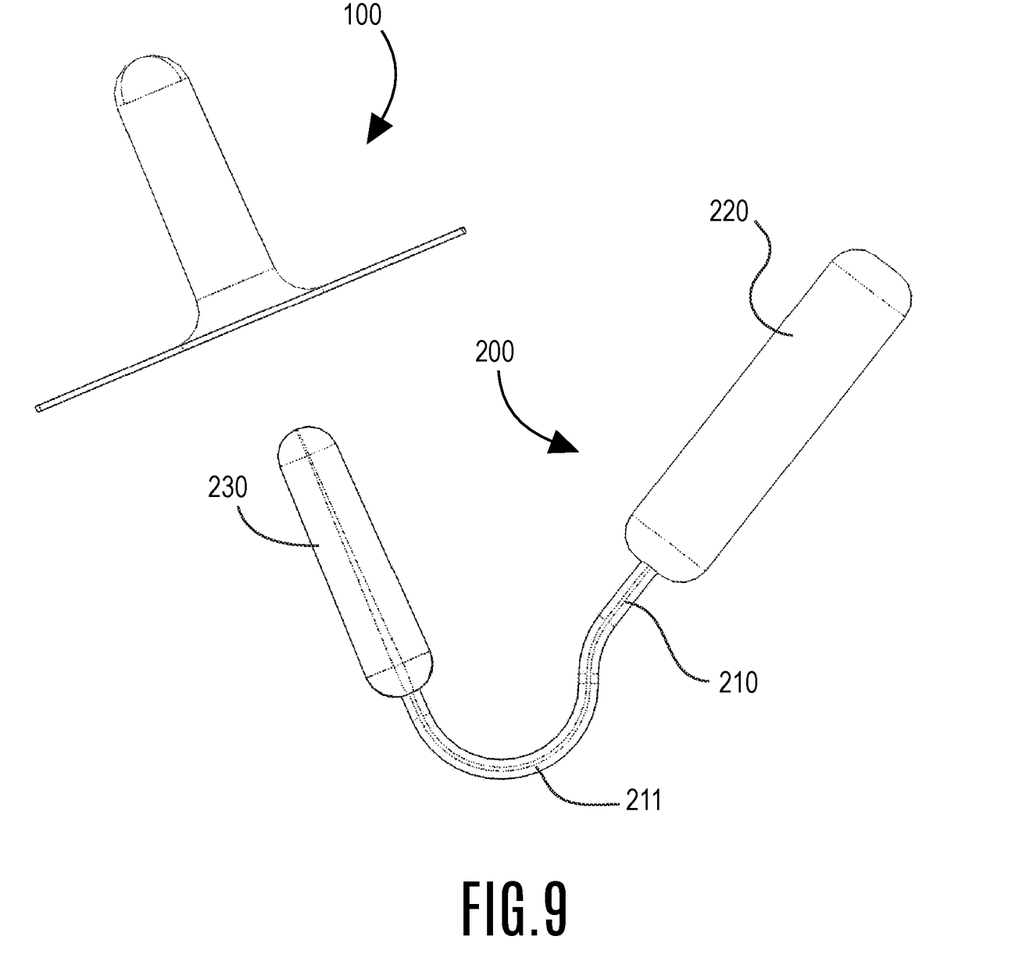
FIG. 9 is a side view of a system including the finger-splinting sheath device and a handle assembly, wherein components of the system are exploded for viewing.

With reference to the drawings, FIG. 9 is a side view of a system including as components: the finger-splinting sheath device (100) and a handle assembly (200), wherein the components of the system are exploded for viewing. Because the finger-splinting sheath device is described above, it will not be further described in the following description. However, the handle assembly (200) comprises a structural-element (210), such as a rod, on which the handle assembly is built. The structural-element may be fabricated from steel, aluminum, plastic, wood, or similar material. Preferably, the structural element is provided pliable shape-retaining component, for example, by fabricating from nitinol or similar material. In this regard, a bend (211) may be configurable to suit user demands. However, in many alternative embodiments, the structural element can be provided in a fixed shape. Here, the structural-element comprises a bend (211) for orienting features of the handle assembly to provide optimized ergonomics for improved use. At a first end of the handle assembly, a gripping-element (220) is formed on, or attached to, the structural-element. The gripping-element is configured to be gripped by a user in a firm and controlling fashion. Additionally, at a second end of the handle assembly opposite the first end, a protruding-element (230) is formed on, or attached to, the structural element. Each of the gripping-element and the protruding-element may comprise an expanded foam formed on respective ends of the structural-element. Alternatively, each of the gripping-element and the protruding-element may comprise attached features, such as molded sub-components, generally including a thermoplastic material or silicone.

Figure 10:
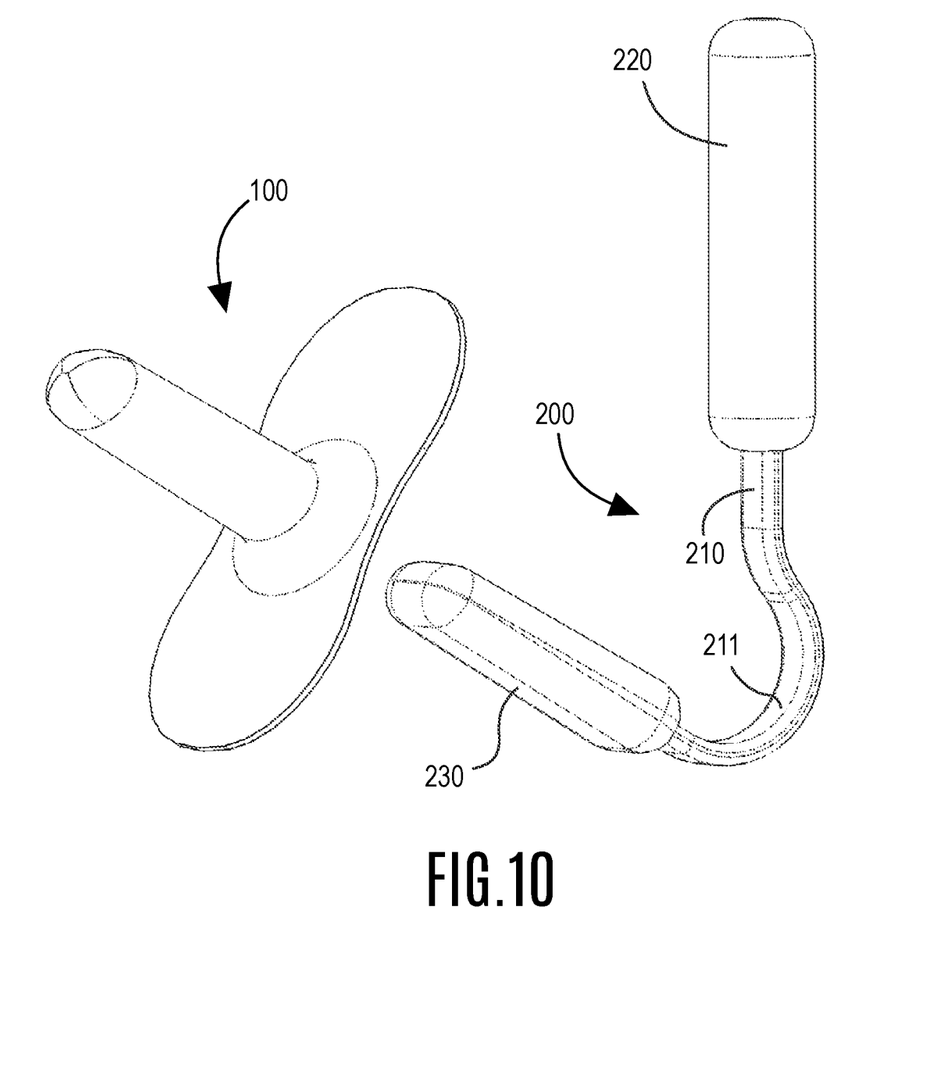
FIG. 10 is a first perspective view of the system in the exploded configuration.

FIG. 10 is a first perspective view of the system in the exploded configuration. Each of the handle assembly (200), structural-element (210), bend (211), gripping-element (220), and protruding-element (230) are further appreciated from the first perspective view.

Figure 11:
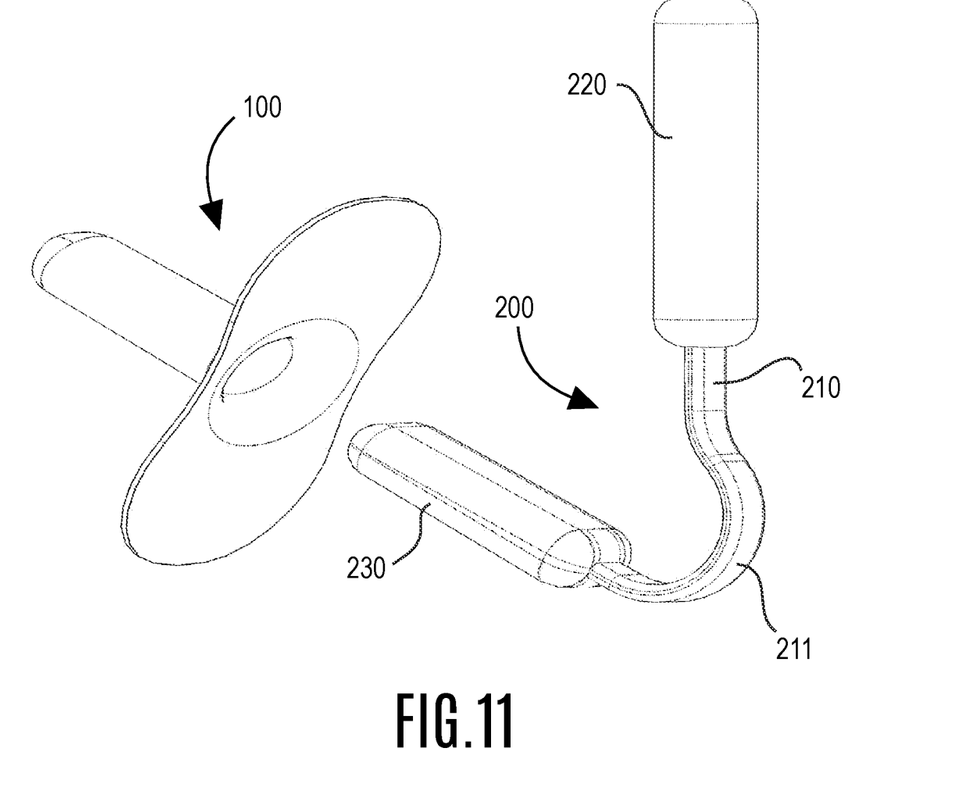
FIG. 11 is a second perspective view of the system in the exploded configuration.

FIG. 11 is a second perspective view of the system in the exploded configuration. Each of the handle assembly (200), structural-element (210), bend (211), gripping-element (220), and protruding-element (230) are further appreciated from the second perspective view.

Figure 12:
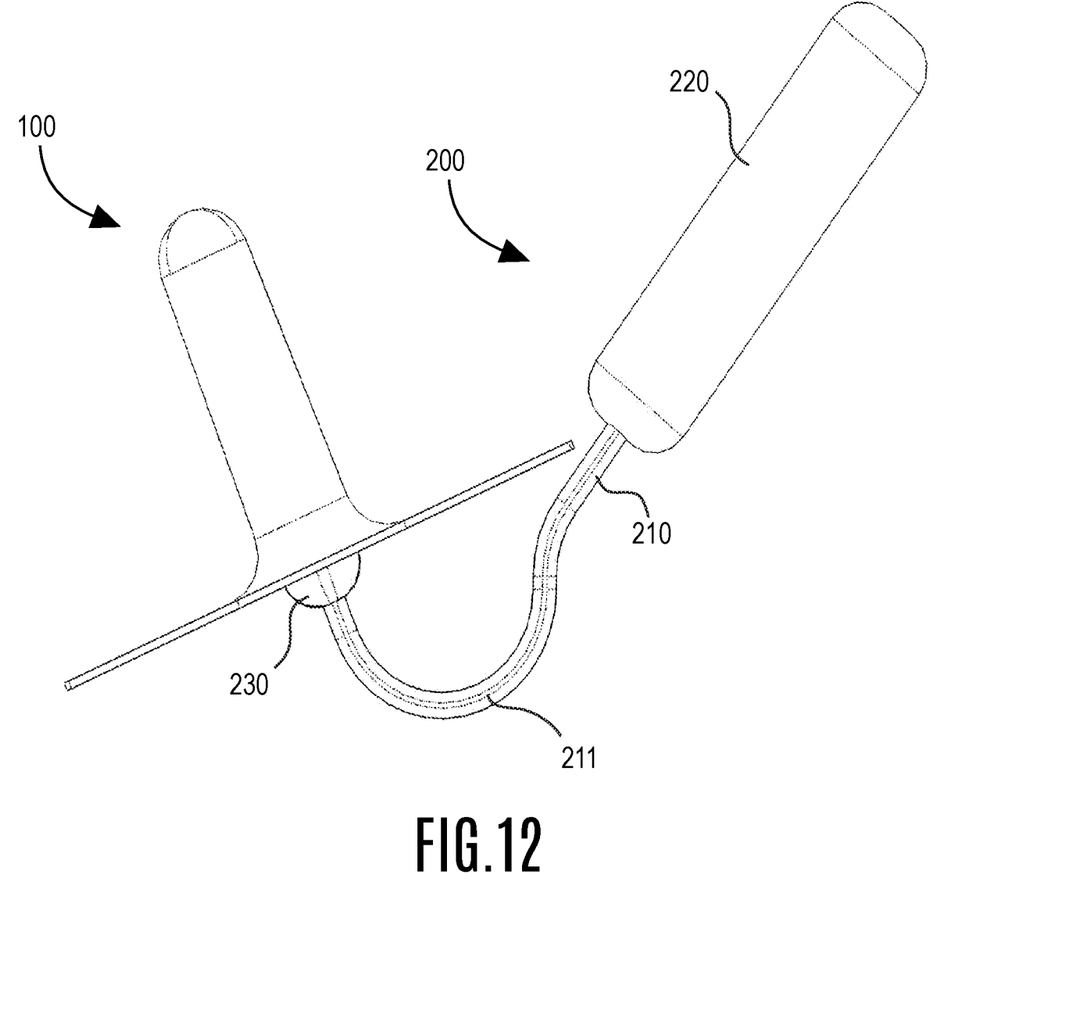
FIG. 12 is a side view of the system in an engaged configuration.

Finally, FIG. 12 is a side view of the system in an engaged configuration. Each of the handle assembly (200), structural-element (210), bend (211), gripping-element (220), and protruding-element (230) are further appreciated in the engaged configuration, where the components are engaged or attached.

Other Features of Embodiments

The embodiment of the finger-splinting sheath device, without the handle assembly, provides an eco-friendly hygienic shield protecting the vagina from pathogens such as germs and bacteria that may be present on hands, under nails, or on jewelry. In addition, the sheath-element is configured to protect nails and jewelry from scratching the vagina and surrounding tissue. Moreover, the device as provided shields nails and jewelry from unwanted exposures, and shields hands from urine and/or body waste. The source of internal vaginal support is derived mostly from inserted fingers and is enhanced by the disclosed device.

In the embodiment of a system including the device and a handle assembly, the system improves range of motion and assists the user with body positioning such that the system can be efficiently and comfortably utilized. Some users may prefer to reach and manage a problem area using the more rigidly structured handle insert for internal vaginal support instead of inserting fingers. In this regard, the source of internal vaginal support will be the handle insert of device referred to herein as the "protruding-element".

While various details, features, and combinations are described in the illustrated embodiments, one having skill in the art will appreciate a myriad of possible alternative combinations and arrangements of the features disclosed herein. As such, the descriptions are intended to be enabling only, and non-limiting. Instead, the spirit and scope of the invention is set forth in the appended claims.

Many women suffering from these conditions and practices find them emotionally debilitating. It has been recognized that digitation can feel undignified for many women, which involves using fingers within the vagina or via the rectum to evacuate stool, and the impact on the lived experience of women who have difficulty with rectal emptying can be significant. The shielding device ameliorates this, allowing enough sensitivity to manage the problem, while protecting from more negative aspects (some of which are described above).

In this regards, utilizing the device, method, and/or system disclosed herein, a subject suffering from complications of pelvic organ prolapse can become empowered for self-management of their disorder.

FEATURE LIST finger-splinting sheath device (100)
flange-element (110)
aperture (111)
indentations (112)
tubular sheath-element (120)
distal end (121)
hollow cavity (122)
handle assembly (200)
structural-element (210)
bend (211)
gripping-element (220)
protruding-element (230)
longitudinal axis ($A_{Lon}$)
lateral axis ($A_{Lat}$)
major axis ($A_{Maj}$)
minor axis ($A_{min}$)
length (L)
periphery (P)
width (W)

What is claimed is:

1. A finger-splinting sheath device, comprising:
a flange-element having an aperture at a center thereof, the flange-element comprising:
a length defined along a longitudinal axis,
a width defined along a lateral axis, and
a periphery having an hourglass-shape with indentations of the periphery being disposed along the lateral axis; and
a tubular sheath-element extending from the aperture of the flange element to a distal end, wherein the tubular sheath-element is closed at the distal end, the tubular-sheath element further comprising a thickness along the lateral axis and a thickness along the longitudinal axis, wherein the thickness along the lateral axis is greater than the thickness along the longitudinal axis.

2. The device of claim 1, wherein the tubular-sheath element extends orthogonally from the flange-element.

3. The device of claim 1, wherein the tubular sheath-element is mechanically biased to extend along a normal axis, wherein the normal axis is orthogonal to each of the longitudinal and lateral axes.

4. The device of claim 1, further comprising a handle assembly, the handle assembly comprising:
a structural-element including at least one bend;
a gripping-element formed on or attached to the structural-element at a first end; and
a protruding-element formed on or attached to the structural-element at a second end opposite the first end,
wherein at least a portion of the protruding element is configured to engage a hollow cavity of the finger-splinting sheath device.

5. The device of claim 1, comprising a thermoplastic elastomer material.

6. The device of claim 1, comprising silicone.

7. The device of claim 1, comprising a semi-rigid material.

8. A finger-splinting sheath device, comprising:
a flange-element having an aperture, the flange-element comprising:
a length defined along a longitudinal axis,
a width defined along a lateral axis, and
a periphery having a first indentation and a second indentation; and
a tubular sheath-element extending from the aperture of the flange element to a distal end, wherein the tubular sheath-element is closed at the distal end, the tubular-sheath element further comprising a thickness along the lateral axis and a thickness along the longitudinal axis, wherein the thickness along the lateral axis is greater than the thickness along the longitudinal axis.

9. The device of claim 8, comprising a semi-rigid material.

10. The device of claim 8, wherein the aperture is disposed between the first indentation and the second indentation.

11. The device of claim 8, wherein the first indentation and the second indentation each comprise a concave portion.

12. The device of claim 8, wherein the first indentation, the second indentation, and the aperture are disposed along the lateral axis.

13. The device of claim 8, wherein the tubular-sheath element extends orthogonally from the flange-element.

14. The device of claim 8, comprising silicone.

15. The device of claim 8, wherein the tubular sheath-element is mechanically biased to extend along a normal axis, wherein the normal axis is orthogonal to each of the longitudinal and lateral axes.

16. The device of claim 8, further comprising a handle assembly, the handle assembly comprising:
   a structural-element including at least one bend;
   a gripping-element formed on or attached to the structural-element at a first end; and
   a protruding-element formed on or attached to the structural-element at a second end opposite the first end,
   wherein at least a portion of the protruding element is configured to engage a hollow cavity of the finger-splinting sheath device.

17. The device of claim 8, comprising a thermoplastic elastomer material.

\* \* \* \* \*